: US 7,857,621 B2
(12) United States Patent  
Teufelberger et al.

(10) Patent No.: US 7,857,621 B2
(45) Date of Patent: Dec. 28, 2010

(54) DENTAL HANDGRIP

(75) Inventors: Gunter Teufelberger, Bürmoos (AT); Hannes Wagner, Salzburg (AT)

(73) Assignee: W&H Dentalwerk Burmoos GmbH (AT)

( * ) Notice: Subject to any disclaimer, the term of this patent is extended or adjusted under 35 U.S.C. 154(b) by 110 days.

(21) Appl. No.: 11/985,873

(22) Filed: Nov. 15, 2007

(65) Prior Publication Data

US 2008/0118887 A1 May 22, 2008

(30) Foreign Application Priority Data

Nov. 16, 2006 (EP) .................................. 06023781
Nov. 16, 2006 (EP) .................................. 06023782

(51) Int. Cl.
*A61C 1/00* (2006.01)
(52) U.S. Cl. .............................. 433/29; 433/88; 433/89
(58) Field of Classification Search .................... 433/80, 433/81, 82, 85, 87, 88, 89, 90, 29; 222/196, 222/196.1, 196.2, 196.3, 196.4, 196.5, 197, 222/198, 199, 200, 201, 202, 203; 601/55, 601/75, 88, 96, 105, 148; 604/22
See application file for complete search history.

(56) References Cited

U.S. PATENT DOCUMENTS

| 3,890,713 | A | | 6/1975 | Nielsen | |
|---|---|---|---|---|---|
| 4,092,778 | A | | 6/1978 | Hirdes | |
| 4,673,353 | A | * | 6/1987 | Nevin | 433/90 |
| 5,125,837 | A | * | 6/1992 | Warrin et al. | 433/98 |
| 5,232,363 | A | * | 8/1993 | Meller | 433/117 |
| 5,908,295 | A | * | 6/1999 | Kawata | 433/29 |
| 6,305,934 | B1 | | 10/2001 | Hatley, Jr. | |
| 6,375,039 | B1 | * | 4/2002 | Anderson | 222/82 |
| 6,848,906 | B2 | * | 2/2005 | Albach | 433/90 |
| 2002/0123020 | A1 | * | 9/2002 | Aumuller et al. | 433/88 |
| 2005/0026106 | A1 | * | 2/2005 | Jefferies | 433/81 |
| 2006/0019220 | A1 | * | 1/2006 | Loebel et al. | 433/215 |

FOREIGN PATENT DOCUMENTS

| DE | 89 04 429 | 11/1989 |
|---|---|---|
| DE | 295 17 958 | 3/1997 |
| FR | 2 190 176 | 6/1978 |
| WO | 01/17454 | 3/2001 |
| WO | 2006/013698 | 12/2006 |

OTHER PUBLICATIONS

European Search Report for EP06027381.
European Search Report for EP06023782.

* cited by examiner

*Primary Examiner*—Cris L Rodriguez
*Assistant Examiner*—Eric Rosen
(74) *Attorney, Agent, or Firm*—Klarquist Sparkman, LLP

(57) ABSTRACT

A dental handgrip for delivering filling compound into a tooth cavity is described, the handgrip being provided with a connection device to which a container for the filling compound can be connected. In some embodiments, the handgrip includes a light emission device via which radiation having a wavelength and radiant power for hardening of filling material can be provided. The dental handgrip can include a safety device to prevent a premature or inadvertent light emission onto the filling compound. In some embodiments, the handgrip includes a fluid-operated feeding device for feeding the filling compound from the filling compound container. A vibration generator operable to cause vibrations in the filling compound and to assist in feeding of the compound can also be provided.

30 Claims, 7 Drawing Sheets

DENTAL HANDGRIP

CROSS REFERENCE TO RELATED APPLICATION

The present application claims priority from pending European Patent Application No. 06023781.5 and European Patent Application No. 06023782.3, both filed Nov. 16, 2006, which are incorporated herein by reference.

BACKGROUND

1. Field

The present application relates to a dental handgrip for delivering filling compound into a tooth cavity.

2. Description of Prior Art

Such a handgrip is known from patent application WO 01/17454 A1. It is used for filling hardenable dental compounds comprising plastic compounds or synthetic resins into previously prepared tooth cavities. The hardening of the plastics or synthetic resins preferably takes place by irradiation with radiation having a wavelength in the range of approximately 320 nm-400 nm or with blue light with a wavelength in the range of approximately 400 nm-470 nm. The radiant power of the radiation usually amounts for example to at least 400 mW/cm$^2$, preferably to more than 900 mW/cm$^2$.

The filling of the tooth cavity and the hardening of the filling compounds is carried out by the dentist in several repetitive steps, each step usually involving the introduction of a layer of filling compound into the tooth cavity, the smoothing of the filling compound layer, if need be the removal of excess filling compound, and the irradiation of the filling compound. Most tooth fillings made of hardenable filling compound thus comprise several layers introduced and hardened one after the other. The filling of a tooth cavity thus represents a costly and time-intensive procedure for the dentist.

There is therefore the object to provide a dental handgrip which simplifies the filling and hardening of a tooth cavity for the dentist, is less time-consuming and offers improved handling.

In the handgrip known from patent application WO 01/17454 A1, the delivery of the filling compound from the filling compound container takes place by manual operation of a lever or similar operating elements. A number of drawbacks are associated with this. The user is not able to concentrate solely on the precisely targeted introduction of the filling compound into the tooth cavity and the shaping and compaction of the filling compound, but rather must turn part of his attention constantly to the delivery of the filling compound. The operating elements, especially when they are designed as levers, require a great deal of space and are troublesome when work is carried out in the spacially limited oral cavity, so that various areas of the oral cavity are accessible only with difficulty using such a handgrip. The operating elements hinder the view of the preparation site. Finally, a uniform delivery of the filling compound is also not guaranteed.

A further object is to provide a dental handgrip for the delivery of filling compound that overcomes these drawbacks. In particular, the dental handgrip is intended to simplify the filling of a tooth cavity for the dentist and to offer improved handling.

SUMMARY

According to a first aspect, a dental handgrip for the delivery of filling compound with a light emission device, via which the radiation can be made available with a wavelength and radiant power suitable for hardening the filling compound, is disclosed. The dentist can thus perform the filling and hardening of the filling material with a single device. The light emission device can comprise at least one light guide, which is designed in particular as a glass rod, glass fibre or glass fibre rod, and/or at least one light source, which is designed in particular as an optical semiconductor element. The energy supply of the light source can take place via a battery or a rechargeable accumulator.

The handgrip is preferably provided with a coupling element, which is used for connecting the light emission device to an external light or energy source. In particular, the coupling element is designed in such a way that it can be coupled to a counter-coupling element, which is provided for the connection to a dental hand-held instrument with another function. Such a counter-coupling element can be provided for example for the connection of a dental turbine, a straight dental handpiece or a contra-angle handpiece or a tartar removal device. The coupling element and counter-coupling element each have at least one light guide or electrical contacts, which lie opposite one another in the coupled state, i.e., are disposed in such a way that a reliable light or energy transmission is guaranteed.

If the dental handgrip additionally has a vibration generator which can be or is connected directly or indirectly to the connection device for the filling compound container, so that the vibration generated by the vibration generator can be transmitted to the filling compound, the coupling element of the handgrip is designed in a particularly preferred example of the embodiment in such a way that it can additionally receive from the counter-coupling element the driving medium for the vibration generator, for example compressed air or electric current. To advantage, the handgrip in these embodiments does not therefore require its own supply device, but can rather be connected to supply devices already available.

In another preferred example of embodiment, the handgrip comprises a first end, at which the connection device for the filling compound container is provided and at which one or more light emission areas of the light emission device can be or are also disposed. To advantage, therefore, the use of the handgrip is additionally facilitated for the dentist. The light emission device can either be provided fixed in the region of the first end, or it can also be arranged so as to be mobile, for example displaceable in the handgrip, so that it can be moved if need be in the direction of the first end or up to the first end or beyond it.

In order to prevent the user from inadvertently delivering filling compound from the filling compound container and directing the light emission device onto the filling compound at the same time, so that for example an undesired, at least partial hardening of the filling compound takes place before the latter has been introduced in the optimum manner into the tooth cavity, the handgrip is provided with a safety device or means to prevent a premature or inadvertent light emission onto the filling compound. These safety means can have the most diverse embodiments, whereby a dental handgrip could have one or more of these safety means. The aim of these safety means is to prevent light from striking the filling compound before the user intends to harden the filling compound, or at least to ensure that the radiant energy or intensity of the light striking the filling compound is so small that a premature hardening reaction caused by the light emission device and disadvantageous to the patient does not take place before the actual hardening is intentionally started by the dentist.

In a first exemplary embodiment, the safety means comprise the light emission area(s) of the light emission device and the delivery opening(s) of the filling compound container, the light emission area(s) and the delivery opening(s) being disposed in such a way that they point in different directions. Alternatively, or additionally, a device, in particular a mechanical device, for example a rotatable or swivelling cover device, can be provided, which is designed in such a way that either only the light emission area(s) or the delivery opening(s) is/are free, so that only light or filling compound can be delivered, whereas the other of the two elements (light emission area or delivery opening) is covered. Instead of the covering of the light emission area, the device can also be designed such that at least the major part of the light emitted by the light emission device is deflected, shielded or absorbed. The essential point is that the means are designed in such a way that no light can arrive at the filling compound as long as this is not desired by the user, or that only so little light strikes the filling compound that it does not lead to a premature, undesired hardening reaction.

In another exemplary embodiment, the safety means comprise a device, in particular a switching device, which is designed in such a way that the delivery device for delivering the filling compound or the light emission device or, respectively, the vibration generator or the light emission device can alternatively be operated. Simultaneous operation or use of the delivery device or the vibration generator and the light emission device is thus prevented, as a result of which a premature, undesired hardening reaction is prevented. The switching device can comprise a large number of different embodiments, whereby it can in principle be designed both purely mechanically, pneumatically, hydraulically, electrically or electronically, or can contain a mixed form of two or more of these embodiments.

The switching device can for example comprise a blocking device, in order to block the delivery device or to interrupt its operation, in particular a mechanical blocking element mobile between the delivery and stop position, especially a pin. In the stop position, for example, the blocking element can block a lever of the delivery device which is to be operated manually. The switching device can also comprise valve elements, for example a mechanically or electrically operated valve, in particular a solenoid valve, which opens or closes a delivery line for the filling compound, or which opens or closes a media line for the operation of the delivery device or the vibration generator. The switching device can comprise electrical switches, which interrupt or produce the current supply for the light emission device. The switching device can also comprise an optical switch, for example an optical shutter device, which interrupts or releases the light conduction of the light emission device.

According to a second aspect, a dental handgrip for the delivery of filling compound with a fluid-operated delivery device for delivering the filling compound from the filling compound container is disclosed, the supply for the handgrip with the driving fluid preferably taking place via an external fluid source. A compressed gas, in particular compressed air, or a liquid, in particular water, can be used as the driving fluid. A coupling element for connecting the delivery device to an external fluid source is preferably also provided on the handgrip, the coupling element particularly preferably being designed in such a way that it can be coupled to a counter-coupling element, which is provided for the connection to a dental hand-held instrument with another function. If the counter-coupling element is part of a dental unit, the quantity of the air fed to the delivery device can be controlled by means of a foot control which is connected to the dental unit. To advantage, the effect of this is that the delivery takes place uniformly and automatically, without the user having to carry out a delivery operation, such as for example operating a lever. All the operating elements for the delivery are not therefore required on the handgrip, so that the user has a better view of the preparation site.

In another exemplary embodiment, the handgrip comprises a vibration generator, which can be or is connected directly or indirectly to the connection device, so that the vibration generated by the vibration generator can be transmitted to the filling compound, as a result of which the viscosity of the filling compound is reduced and the filling compound can be delivered more easily. The vibration generator is designed as a fluid-operated vibration generator. The vibration generator and the delivery device are preferably connected to one another directly or indirectly, for example via the hollow vibration shaft of the vibration generator, so that at least a part of the fluid can be used for the operation of the delivery device and the vibration generator. A handgrip according to this embodiment is constructed very simply and compactly, especially in terms of production and assembly, as a result of which the production and assembly costs can be significantly reduced. Such a handgrip also uses the driving fluid effectively and sparingly. The connection between the vibration generator and the delivery device can of course also take place via one or more lines, channels, holes or other elements. The connection can also contain other functional elements, such as for example valves, in particular for the pressure control.

Different devices for the filling of cavities with a filling material are explained below with the aid of preferred examples of embodiment and by reference to the appended drawings:

DETAILED DESCRIPTION

Figure 1:
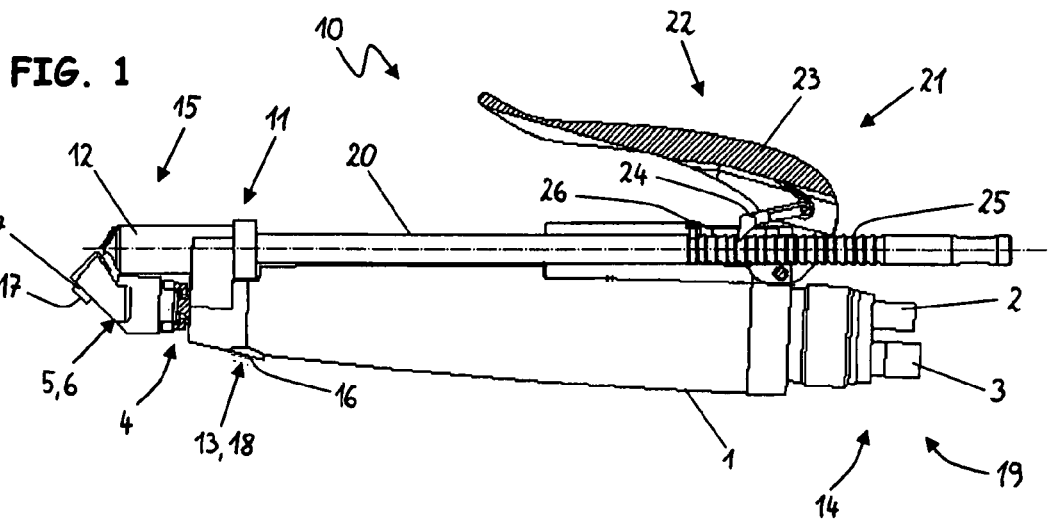
FIG. 1 shows a first example of embodiment of a dental handgrip for the delivery of filling compound with a vibration transmitter for transmitting vibrations to the filling compound container, the vibration transmitter being connected detachably to the handgrip.
Figure 2:
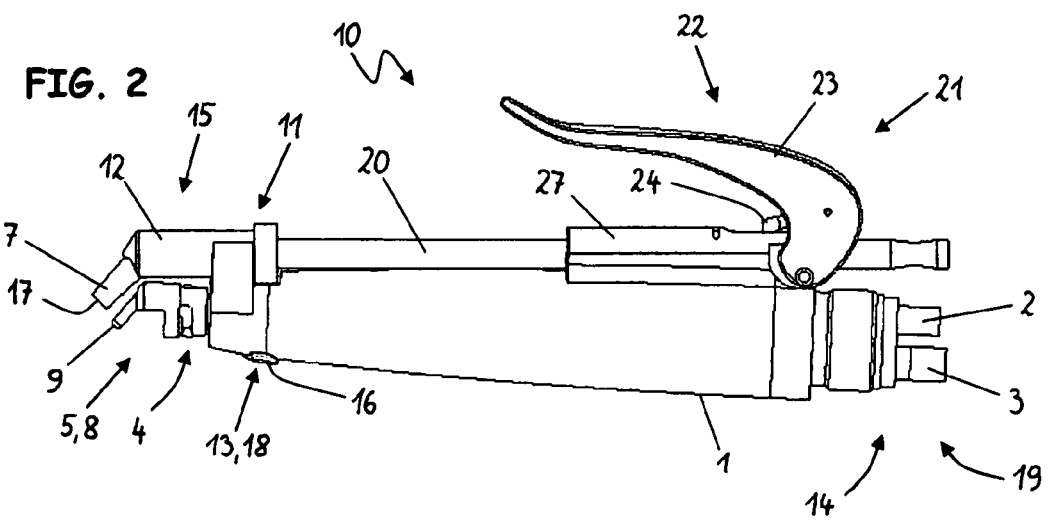
FIG. 2 shows the dental handgrip from FIG. 1 with a probe which can be caused to vibrate, the probe being connected to the handgrip instead of the vibration transmitter.

The dental handgrip 10 represented in FIGS. 1 and 2 for delivering filling compound into a tooth cavity comprises an elongated, essentially cylindrical body with an outer sleeve 1 with a first end 15 and a second end 19. Provided at second end 19 is a coupling element 14, which is preferably designed in such a way that it can be coupled to a counter-coupling element, which is provided for the connection to a dental hand-held instrument with another function. This dental hand-held instrument can in particular be a compressed air-driven turbine handpiece or a tartar removal handpiece. Coupling element 14 comprises at least a first connection 2 to a fluid source, preferably a compressed gas source, in particular to a compressed air source, whereby the fluid can be fed via a line disposed in the interior of handgrip 10 or via channels to a vibration generator (not shown). After passing through the vibration generator, the fluid can be discharged again from handgrip 10 via connection 3. A liquid, preferably water, can of course also be used as a fluid.

The fluid drives the vibration generator, which is connected directly or indirectly to a connection device 4 and a tool 5 accommodated therein, so that tool 5 can be caused to vibrate. The vibration generator can for example comprise an impeller, a sleeve which can be caused to rotate and which surrounds a vibration shaft, or a sphere or disc which is accommodated in a chamber and can be set into motion.

Connection device 4 is designed as a detachable connection device, preferably as a quick-action coupling, in particular as a bayonet coupling, so that different tools 5 can be connected to it. As tool 5, FIG. 1 shows by way of example the vibration transmitter or sonotrode 6, the first end whereof can be connected detachably to connection device 4 and the second end whereof makes contact with filling compound container 12. The second end of sonotrode 6 can have different forms, for example an offset, a groove or a hole. The essential point is that a contacting connection between the second end of vibration transmitter 6 and at least a part of filling compound container 12, for example dispensing tube 7, is produced, so that the vibration of the vibration generator is transmitted to container 12 and the filling compound located therein, as a result of which the filling compound can be introduced more easily into the tooth cavity on account of the change in viscosity produced by the vibration.

In FIG. 2, tube 5 inserted into connection device 4 is designed as probe 8, which the dentist uses for the smoothing, plugging, shaping or compacting of the filling compound introduced into the tooth cavity. Probe 8 in turn has a first end, which can be connected detachably to connection device 4, and a second end or working end 9. Working end 9, which is used for the smoothing, plugging, shaping or compacting, can have different shapes, with for example round, spherical, oval, stepped, wedge-shaped or tapering regions, or can be embodied as shown for example in FIGS. 13-15. Probe 8 can be caused to vibrate through the connection with the vibration generator, so that a much better work result is achieved than with the use of a conventional probe guided by hand.

The advantage of connection device 4 consists in the extended applicability of handgrip 10 for the filling of the cavity with filling compound and subsequent optimised post-treatment of the filling compound with probe 8 which can be caused to vibrate. In order to perform the two tasks, it is merely necessary to exchange the two tools 6, 8.

Handgrip 10 also comprises a light emission device 13 with a light emission area 16, which emerges in the region of first end 15 of handgrip 10 through an opening in outer sleeve 1. Light emission area 16 is formed by the end of a light guide 18, for example a glass rod or glass fibre rod. Light emission device 13 also comprises a light source disposed in handgrip 10, said light source emitting radiation with a wavelength and radiant power for the hardening of filling material, for example an optical semiconductor element, and an energy source, for example one or more batteries, accumulators or a generator for supplying the light source. A handgrip is thus created, for the operation which it is sufficient to connect the latter to a fluid source and which is independent of other media sources, in particular an energy source. It is however also possible, of course, to provide coupling element 14 with electrical contacts, so that the energy supply of the light source takes place for an external energy source, or to equip coupling element 14 with a light guide, so that the handgrip can be supplied with radiation from an external radiation source. Instead of the light guide, the light source can also be provided close to the opening of outer sleeve 1, so that light emission area 16 is designed as part of the light source.

In a particularly preferred embodiment, handgrip 10 can thus be used to perform three functions, namely the filling-in of filling compound into a cavity, the post-treatment of the filling compound with probe 8 which can be caused to vibrate and the hardening of the filling compound. However, simpler embodiments are of course also possible, wherein only two of the three functions can be performed by means of the handgrip, for example filling and post-treatment of the filling compound, filling and hardening of the filling compound or post-treatment and hardening of the filling compound. Each of these embodiments simplifies the restoration of a tooth cavity for the dentist and makes it less time-consuming.

Handgrip 10 is provided with a feeding device 21, which can be operated manually by the user. Feeding device 21 comprises a slide rod 20, which can be moved by means of a forward-thrust mechanism 22 in the direction of first end 15 of handgrip 10. Forward-thrust mechanism 22 comprises a swivelling lever 23, an engagement element 24 pretensioned by means of a spring, said engagement element 24 being connected in a rotary manner to lever 23, for example a catch with a wedge-shaped front end, and a section 25 of the slide rod 20 provided with teeth, into which engagement element 24 engages.

The forward movement of slide rod 20 in the direction of first end 15 takes place by means of a back and forth movement of lever 23, whereby, by the swivelling of lever 23 in the direction of first end 15 and the movement of engagement element 24 thus caused, slide rod 20 is also moved in the direction of first end 15. By the swivelling of lever 23 in the direction of second end 19, engagement element 24 is also shifted in this direction, as a result of which it engages in another tooth of section 25 located closer to end 19. A spring 26, which surrounds slide rod 20 in its section 25, prevents an undesired slipping-back of slide rod 20 during the swivelling of lever 23 in the direction of second end 19. The backward movement of slide rod 20 in the direction of second end 19 takes place by pulling slide rod 20, the latter preferably having, at the end pointing in the direction of second end 19 of handgrip 10, a grip element, for example in the form of a grip pattern or an offset.

Forward-thrust mechanism 22 can of course also be designed differently, for example with a rotary knob or a displaceable slide instead of lever 23 or one or more toothed wheels instead of catch-shaped engagement element 24. Parts of feeding device 21, in particular toothed section 25, can be covered by a housing 27.

A connection device 11 for a filling compound container 12 is provided at first end 15 of handgrip 10. Connection device 11 can be designed in different ways, for example as a plug-in connection, a clamp connection or as a quick-action connection, in particular as a bayonet connection. Filling compound container 12 has an interior space in which the filling compound is accommodated, a delivery opening 17 through which the filling compound can exit, and a mobile, displaceable rear wall. If feeding device 21 is operated, slide rod 20 moves in the direction of connection device 11 until it reaches the rear wall of filling compound container 12. The rear wall is also shifted in the direction of delivery opening 17 by driving slide rod 20 further forwards, as a result of which the filling compound is pressed out of container 12.

Figure 5:
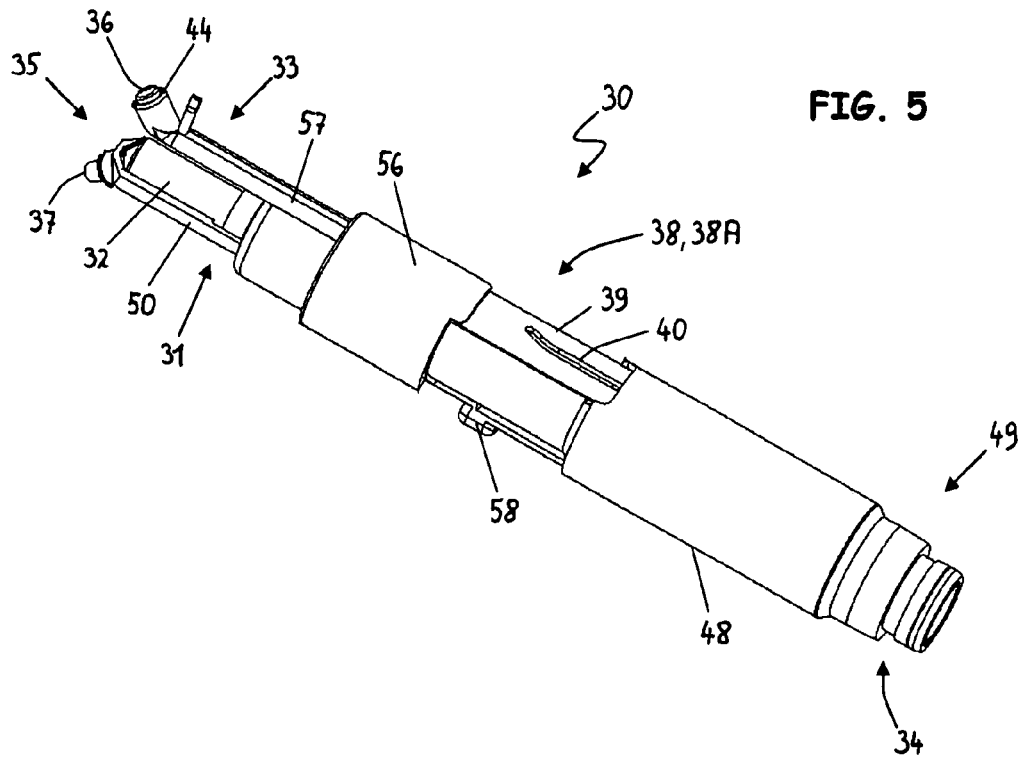
FIG. 5 shows a second exemplary embodiment of a dental handgrip for the delivery of filling compound with a manually displaceable delivery device for delivering the filling compound.
Figure 6:
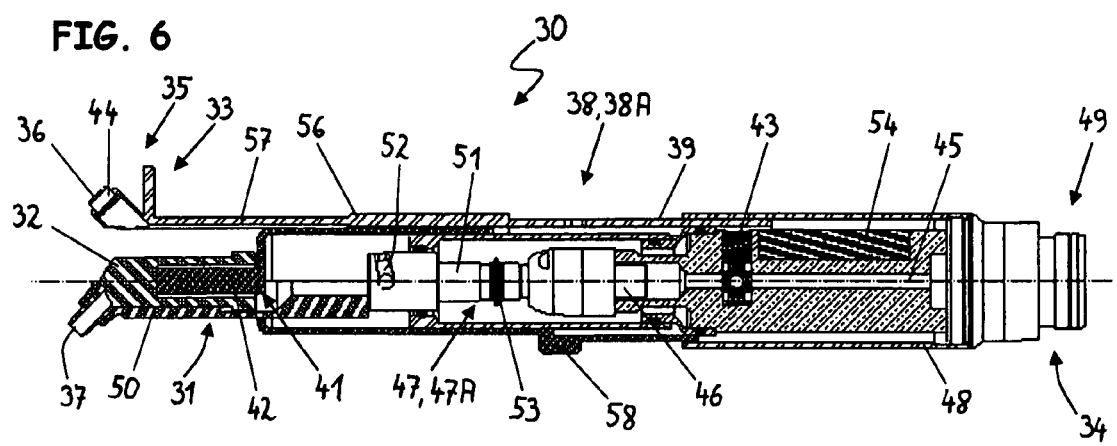
FIG. 6 shows a cross-sectional representation of the handgrip from FIG. 5 with the light emission device shifted forwards and with the delivery device shifted forwards.
Figure 7:
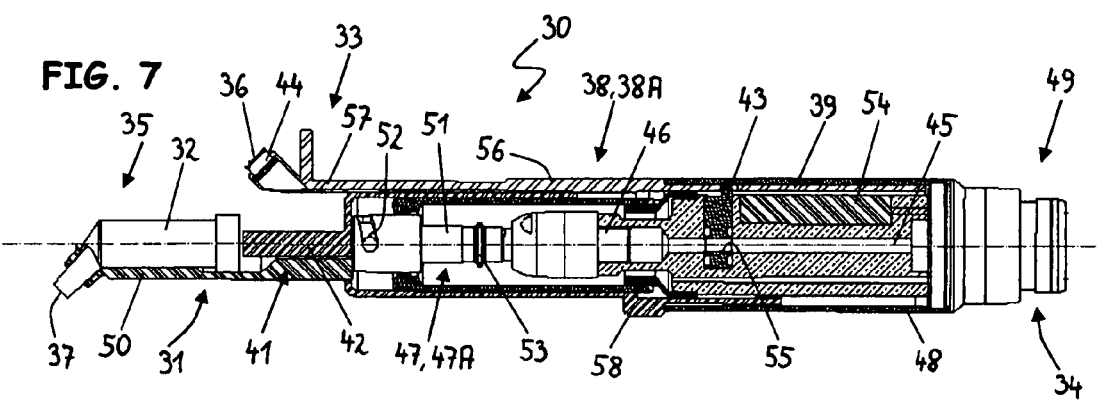
FIG. 7 shows a cross-sectional representation of the handgrip from FIG. 5 with the light emission device shifted backwards and with the delivery device shifted backwards.
Figure 8:
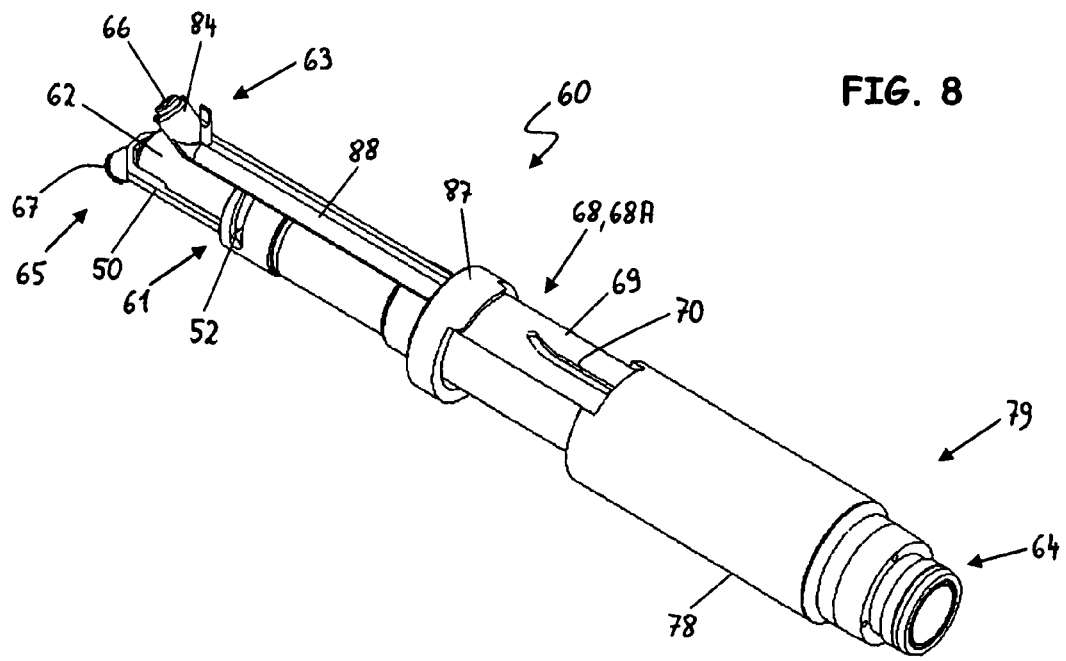
FIG. 8 shows a third exemplary embodiment of a dental handgrip for the delivery of filling compound with a pneumatically operated delivery device for delivering the filling compound and a pneumatically operated vibration generator.
Figure 9:
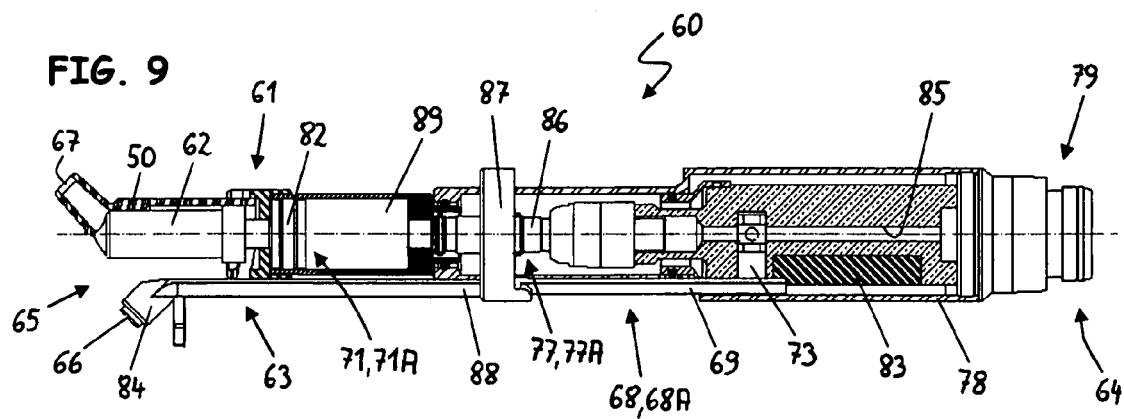
FIG. 9 shows a cross-sectional representation of the handgrip from FIG. 8 with the light emission device shifted forwards and with the delivery device shifted forwards.
Figure 10:
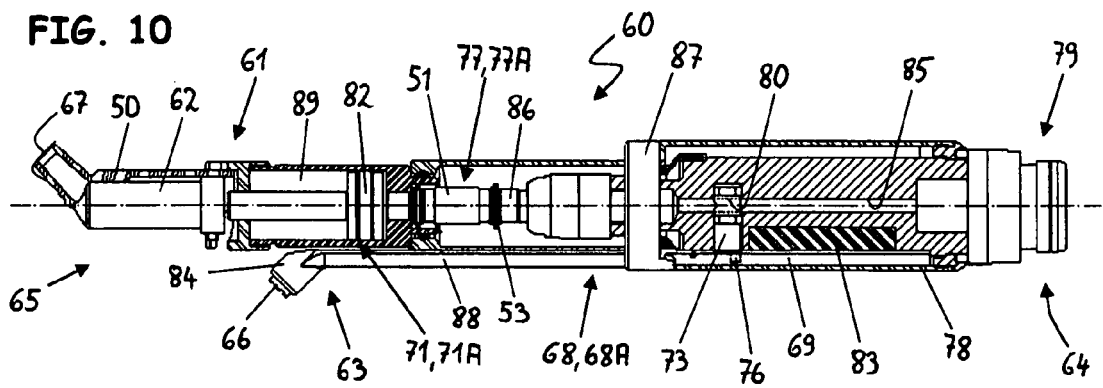
FIG. 10 shows a cross-sectional representation of the handgrip from FIG. 8 with the light emission device shifted backwards and with the delivery device shifted backwards.

FIGS. 5-7 show a second embodiment of a dental handgrip 30 for the delivery of filling compound into a tooth cavity and FIGS. 8-10 show a third embodiment of such a dental handgrip 60. Identical components are described jointly in the following for both handgrips 30, 60.

Handgrips 30, 60 comprise an elongated, essentially cylindrical body with an outer sleeve 48, 78 and have a first end 35, 65 and a second end 49, 79. Provided at second end 49, 79 is a coupling element 34, 64, which is preferably designed in such a way that it can be coupled to a counter-coupling element, which is provided for the connection to a dental hand-held instrument with another function. This dental hand-held instrument can in particular be a compressed air-driven turbine handpiece or a tartar removal handpiece or an electrically operated straight or contra-angle handpiece or a dental small-power motor, in particular an electric motor.

Coupling element 34, 64 has at least one connection to a fluid source, from which a fluid line 45, 85 leads into handgrip 30, 60. Coupling element 34, 64 also has at least two electrical contacts, from which electrical lines lead to at least one consumer in handgrip 30, 60. Coupling element 34, 64 can be designed in different ways, for example as a plug-in coupling, a bayonet coupling or as a screw coupling, but preferably it is designed as a rotary plug-in coupling.

Figure 19:
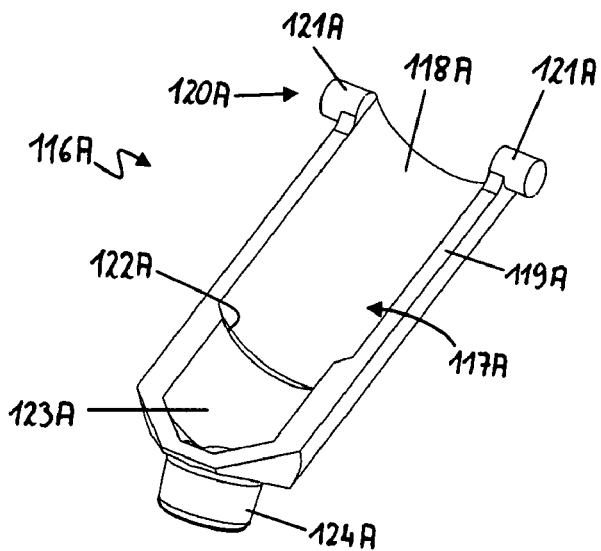
FIG. 19 shows a first embodiment of a connection device for a filling compound container with a short dispensing tube.
Figure 20:
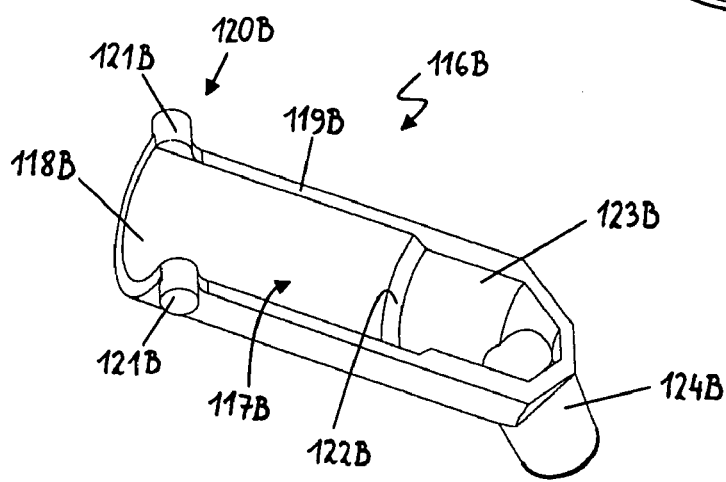
FIG. 20 shows a second embodiment of a connection device for a filling compound container with a long dispensing tube.
Figure 21:
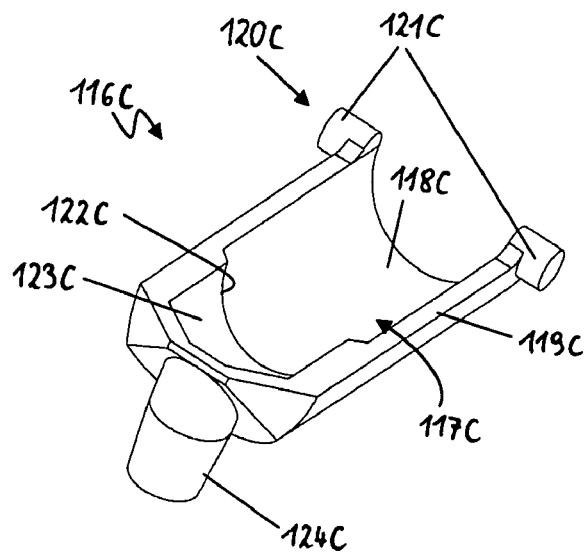
FIG. 21 shows a third embodiment of a connection device for a filling compound container with a dispensing tube disposed approximately at right angles to the carrier part.

A first connection device 31, 61 for a filling compound container 32, 62 is provided at first end 35, 65 of handgrip 30, 60. Connection device 31, 61 can be designed in different ways, for example as a plug-in connection, a clamp connection or as a quick-action connection, in particular as a bayonet connection 52. Connection device 31, 61 preferably comprises a sonotrode 50, which is preferably designed as a holder, in particular as an elongated holder provided with a base and an edge running around the latter, in which holder filling compound container 32, 62 can be inserted, plugged in or fixed in some other way. Sonotrode 50 can be designed for example as shown in FIGS. 19-21.

Connection device 31, 61 and in particular sonotrode 50 are connected to a vibration generator 47, 77 disposed inside handgrip 30, 60. Vibration generator 47, 77 can be designed as an electrical vibration generator, for example as a piezo-element or as a magnetostrictive element, or preferably as a fluid-operated vibration generator 47A, 77A. Fluid-operated vibration generator 47A, 77A can for example comprise an impeller or a sphere or disc accommodated in a chamber and able to be set in motion and can be operated with compressed gas or with a liquid. In the embodiments shown in FIGS. 5-10, vibration generator 47A, 77A is operated with compressed air and comprises a hollow vibration shaft 46, 86, which is connected to fluid line 45, 85. Compressed air flows into vibration shaft 46, 86 and exits through holes in vibration shaft 46, 86. A rotary sleeve 51 is disposed over the holes and is caused to rotate by the exiting compressed air in such a way that vibration shaft 46, 86 is caused to vibrate. O-rings 53 limit the axial movement of rotary sleeve 51. The air that has exited through the holes flows through intermediate spaces or lines in the interior of handgrip 30, 60 back in the direction of coupling element 34, 64.

Handgrip 30, 60 is provided with a light emission device 33, 63, which comprises a light source 44, 84, for example at least one optical semiconductor element, in particular at least one LED. Light source 44, 84 is connected via electrical lines in the interior of handgrip 30, 60 to the electrical contacts of coupling elements 34, 64. Light source 44, 84 emits radiation with a wavelength and a radiant power which is suitable for hardening filling material.

Light emission device 33, 63, in particular light emission area 36, 66 of light emission device 33, 63, is or can be preferably disposed at first end 35, 65 of handgrip 30, 60, where filling compound container 32, 62 is also located. This arrangement offers the user the advantage of simple handling of handgrip 30, 60, but it also involves the risk of filling compound being inadvertently delivered from filling compound container 32, 62 and light emission device 33, 63 at the same time irradiating light onto the filling compound, so that the filling compound is hardened, although the latter is for example not yet in its desired place or is not yet distributed in the optimum manner in the tooth cavity. In order to minimise this risk, dental handgrip 30, 60 can have one or more safety measures or devices to prevent a premature or inadvertant light emission onto the filling compound.

These safety means can comprise any of a large number of different measures and devices. Thus, light emission area(s) 36, 66 of light emission device 33, 63 and delivery opening(s)

37, 67 of filling compound container 32, 62 can be disposed in such a way that they point in different directions. The essential point is that the power of the radiation striking the filling compound is at least so small that a premature hardening reaction disadvantageous to the patient does not occur due to the light emission device before the actual hardening intentionally started by the dentist.

As a safety means of handgrip 30, 60, provision is also made to fit light emission device 33, 63 to handgrip 30, 60 in a mobile manner, for example in a rotatable, foldable or displaceable manner. Light emission device 33, 63 can thus be moved between a first position, in which the light emission onto the filling compound is at least made difficult or impossible for the user or the radiant power striking the filling compound is reduced as described above, and a second position, in which the sighting and aiming with the light emission device 33, 63 and the emission of the radiation onto the filling compound is favoured and simplified, so that a radiant power sufficient for the hardening strikes the filling compound. In the embodiments of FIGS. 5-10, light emission device 33, 63 designed as LED 44, 84 is fixed on a carrier device, for example a rod-shaped carrier 57, 88, which is disposed in a displaceable manner on handgrip 30, 60. In the region of second end 49, 79; an intermediate space is provided between outer sleeve 48, 78 and the components accommodated in the interior of handgrip 30, 60, so that rod-shaped carrier 57, 88 can be introduced into this intermediate space. LED 44, 84 can thus be disposed in a first position represented in FIGS. 6 and 9, in which it is essentially located at first end 35, 65 of handgrip 30, 60 and in which the user can harden the filling compound introduced into the tooth cavity in a straightforward manner and with sufficient radiant power, or it can be disposed in a second position represented in FIGS. 7 and 10, in which it is remote from first end 35, 65 of handgrip 30, 60, so that the hardening of the filling compound is made difficult for the user.

A further safety means of handgrip 30, 60 comprises a device 38, 68, in particular a switching device 38A, 68A, which is designed in such a way that only vibration generator 47, 47A, 77, 77A or light emission device 33, 63 can alternatively be operated. Switching device 38A, 68A preferably has at least one common switching element 39, 69 for vibration generator 47, 77 and light emission device 33, 63, whereby switching element 39, 69 is designed in particular as a gate element 40, 70 with a guide slot 74.

Switching element 39, 69 comprises electrical contacts, which are or can be connected via electrical lines to light emission device 33, 63 in the form of a light source 44, 84, in particular at least one LED, and supply the latter with current. Switching element 39, 69 is fixed to handgrip 30, 60 between at least two positions in a mobile manner, for example in a displaceable, rotatable or swivellable manner, whereby switching element 39, 69 and the electrical contacts are designed and/or disposed in such a way that they are connected to the at least two electrical contacts of coupling element 34, 64 in one of the two positions and are separated from these contacts in the other of the two positions, so that light emission device 33, 63 can be switched on or off by operating switching element 39, 69.

Figure 11:
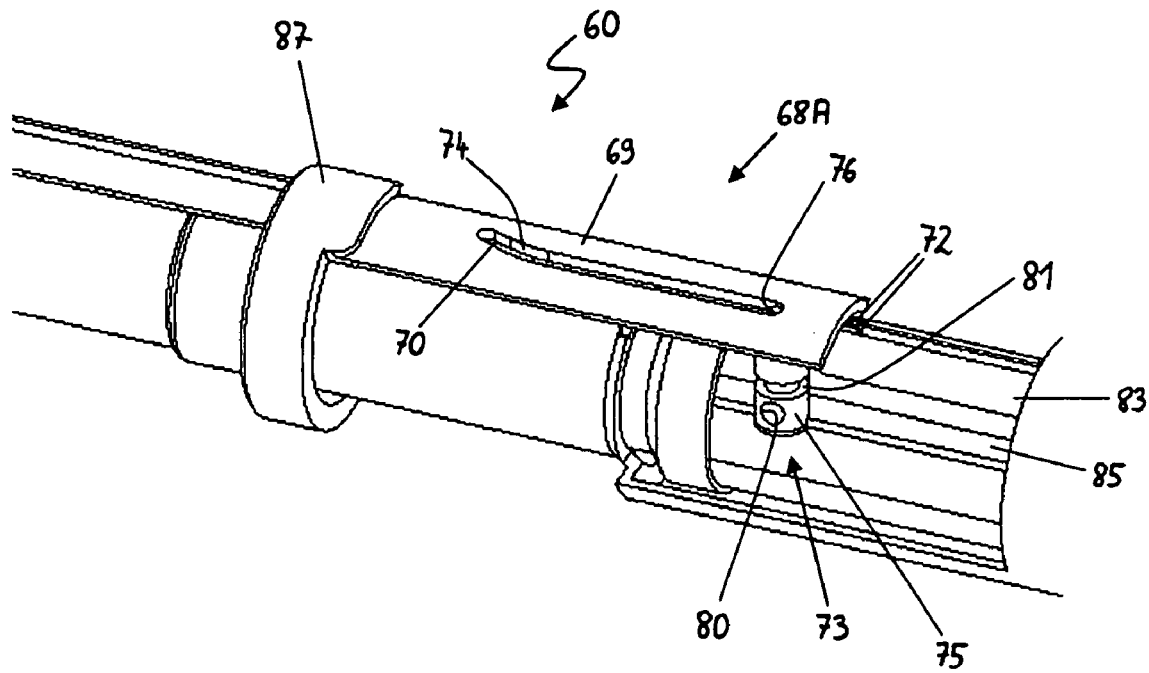
FIG. 11 shows an enlarged representation of the switching device of the handgrip from FIG. 8, the switching position for the operation of the light emission device being selected.

In order to make available the required operating current to light emission device 33, 63, an electrical supply unit 54, 83 is provided in handgrip 30, 60. Said supply unit contains known electrical or electronic components such as transformers, diodes etc., in order to prepare the current obtained from the energy source, in particular the current intensity, type of current or level of current etc. for light emission device 33, 63. As can be seen in particular from FIGS. 11 and 12, supply unit 54, 83 can also contain electrical switching contacts, via which the current supply of light emission device 33, 63 can be switched on or off with the electrical switching contacts of switching element 39, 69. According to the embodiment of FIGS. 6, 7 and 9, 10, electrical switching contacts 72 are disposed at the end of supply unit 54, 83 facing first end 35, 65 of handgrip 30, 60 and the switching contacts of switching element 39, 69 at the end of switching element 39, 69 facing second end 49, 79 of handgrip 30, 60. In FIGS. 6, 9 and 11, switching element 39, 69 assumes a position shifted in the direction of first end 35, 65, so that the switching contacts of switching element 39, 69 are disposed over contacts 72, are in contact with the latter, and the current circuit for light emission device 33, 63 is closed. In this position, light emission device 33, 63, which to advantage is connected to switching element 39, 69, is also shifted forwards, to first end 35, 65 of handgrip 30, 60, so that optimum handling of handgrip 30, 60 is guaranteed for the user during hardening.

Figure 12:
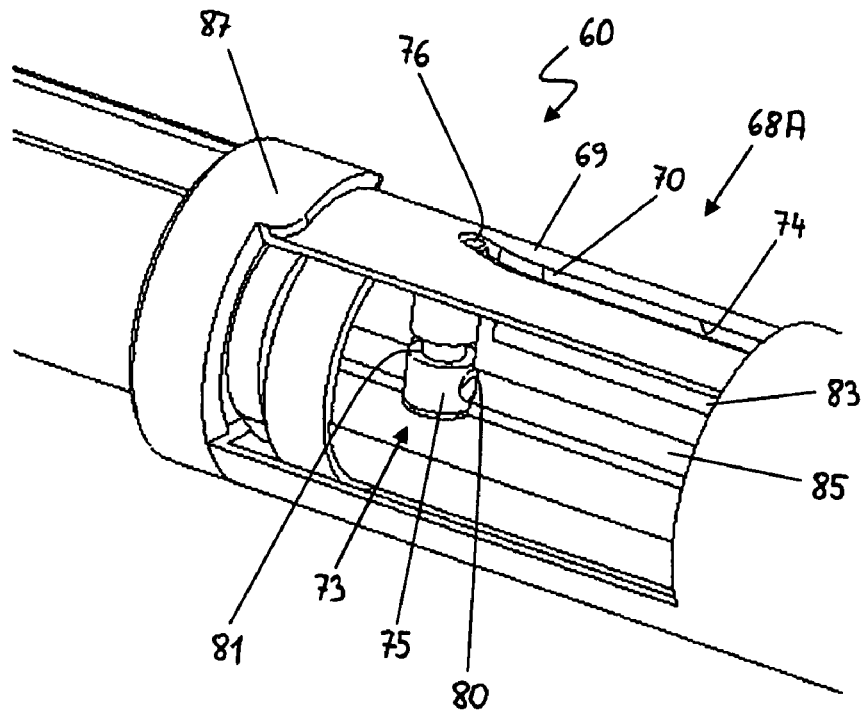
FIG. 12 shows an enlarged representation of the switching device of the handgrip from FIG. 8, the switching position for the pneumatic operation of the delivery device and the vibration generator being selected.

In FIGS. 7, 10 and 12, switching element 39, 69 assumes a position shifted in the direction of second end 49, 79, so that the switching contacts of switching element 39, 69 are remote from contacts 72 and the current circuit for light emission device 33, 63 is interrupted. At the same time, light emission device 33, 63 is also shifted in the direction of second end 49, 79.

Figure 3:
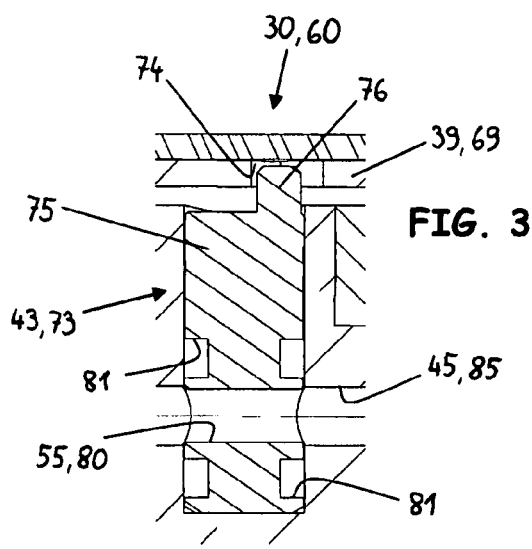
FIG. 3 shows a first exemplary embodiment of a valve as part of a switching device disposed in the handgrip, by means of which valve the delivery device for delivering the filling compound or, respectively, the vibration generator or the light emission device can alternatively be operated.

Switching device 38A, 68A with switching element 39, 69 is also designed in such a way that a blocking element, preferably a valve 43, 73, can be operated via switching element 39, 69, said blocking element interrupting the supply of vibration generator 47, 77 with a driving medium. In the embodiments represented in FIGS. 6, 7, 9, 10 and 11, 12, vibration generator 47A, 77A is supplied with compressed air via fluid line 45, 85. As can be seen in particular from FIG. 3, valve 43, 73 comprises a cylindrical valve body 75 disposed in a rotatable manner in handgrip 30, 60, with a through-hole 55, 80 and a pin 76 fixed eccentrically on valve body 75, said pin being accommodated in slot 74 of switching element 39, 69. Guide slot 74 is designed in an angular or curved manner, so that valve body 75 is rotated via eccentric pin 76 by the shifting of switching element 39, 69, so as to assume a first position in which hole 55, 80 is aligned with fluid line 45, 85, so that the compressed air can pass through valve 43, 73 in the direction of vibration generator 47A, 77A (see FIG. 12), or so as to assume a second position in which hole 55, 80 is facing away from fluid line 45, 85, so that the connection between the compressed air source and vibration generator 47A, 77A is interrupted (see FIG. 11). One or more grooves 81 are provided on valve body 75 in order to accommodate sealing elements, in particular O-rings.

Guide slot 74 is designed in such a way and/or is disposed on switching element 39, 69 in such a way that, in the position in which switching element 39, 69 is shifted such that the current circuit for light emission device 33, 63 is closed, hole 55, 80 is facing away from fluid line 45, 85, so that the connection between the compressed air source and vibration generator 47A, 77A is interrupted, or in such a way that, in the position in which switching element 39, 69 is shifted such that the current circuit for light emission device 33, 63 is opened, hole 55, 80 is facing fluid line 45, 85, so that the connection between the compressed air source and vibration generator 47A, 77A is passable. Switching device 38, 38A, 68, 68A is thus designed in such a way that either vibration generator 47A, 77A or light emission device 33, 63 are alternatively active. Particularly in the case of the use of highly viscous filling compounds, which can only be introduced with great difficulty into a tooth cavity without the operation of a vibration generator 47A, 77A, it is thus sufficiently guaranteed that either only the filling compound from container 32, 62 is removed or light emission device 33, 63 is operated.

For the purpose of simple operation, switching element 39, 69 is connected to an actuating element 56, 87. Actuating element 56 can have the most diverse embodiments, for example a displaceable sleeve wholly or partially surrounding handgrip 30, 60.

Figure 4:
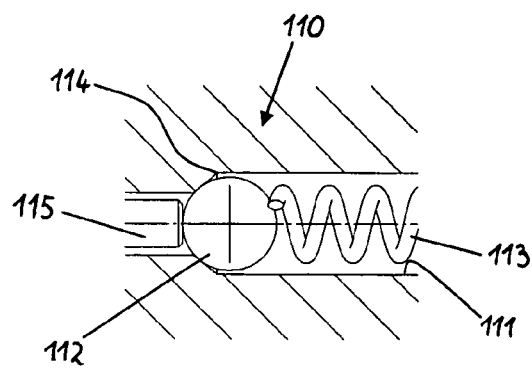
FIG. 4 shows a second exemplary embodiment of a valve as part of a switching device disposed in the handgrip, by means of which valve the delivery device for delivering the filling compound or, respectively, the vibration generator or the light emission device can alternatively be operated.

Instead of previously described valves 43, 73, other blocking elements can of course also be used, such as for example slides or flaps, in particular other electrical or mechanical valves. FIG. 4 shows, by way of example, one such valve, which is designed as a ball valve 110. Compressed air line 111 has two sections with different diameters, which are connected by a tapering section forming a shoulder 114. In compressed air line 111, a valve body 112, which is designed for example as a ball, is pressed by a spring 113 against shoulder 114, so that compressed air line 111 is closed and no compressed air can pass to the vibration generator and/or the feeding device. By operating the switching device, for example switching device 38A, 68A, a piston 115 disposed in compressed air line 111 pushes valve body 112 against the spring tension of spring 113, so that valve body 112 is spaced apart from shoulder 114 and compressed air can pass through valve body 112.

The components embodied in different ways with handgrips 30, 60 are described in the following.

Handgrip 30 comprises a feeding device 41 for feeding the filling compound out of container 32 in the direction of the tooth cavity or into the tooth cavity. Feeding device 41 comprises a feeding element 42, for example a piston, shaft, ram or stamp, which is disposed on handgrip in a mobile manner. Filling compound container 32 has an interior space in which the filling compound is accommodated, a delivery opening 37 through which the filling compound can exit, and a mobile, displaceable rear wall. If feeding device 41 is operated, feeding element 42 moves in the direction of connection device 31 until it reaches the rear wall of filling compound container 32. As a result of driving feeding element 42 further forwards, the rear wall is also shifted in the direction of delivery opening 37 and feeding element 42 moves into connection device 31 and enters the filling compound container 32, so that the filling compound is pressed out of container 32.

The movement of feeding element 42 takes place manually with handgrip 30, i.e., by the user. For this purpose, feeding element 42 is connected to an actuating element 58, which is fitted on handgrip 30 so as to be able to be operated by the user. Actuating element 58 is designed as a slide, which is connected via a sleeve to feeding element 42. Actuating element 58 can however also have other forms and can for example be designed as a swivelling lever or rotary knob.

In contrast with this, handgrip 60 represented in FIGS. 8-10 comprises a feeding device 71 operated by means of an energy source, said feeding device preferably being designed as a fluid-operated feeding device 71A. As a driving fluid, use can be made for example of water or compressed gas, preferably compressed air, which is made available from external media sources. Feeding device 71, 71A comprises a feeding element 82 which can be shifted by the fluid in the direction of connection device 61, for example a piston, shaft, ram or stamp, which is disposed on handgrip 60 in a mobile manner. The return of feeding element 82 from the position in which it has penetrated farthest into container 62 and/or connection device 61, shown in FIG. 9, into the initial position shown in FIG. 10 can take place automatically by means of a spring element or by means of an actuating element operated by the user. The feeding of the filling compound from container 62 takes place in the same way as described above for handgrip 30.

Vibration generator 77, 77A of handgrip 60 is particularly preferably operated with the same fluid, i.e., the same fluid stream or part of fluid stream, as feeding device 71, 71A. This results in a particularly advantageous, simple construction of handgrip 60, which comprises for example a common fluid line 85 for vibration generator 77A and feeding device 71, 71A. In addition, vibration generator 77, 77A can be connected directly or indirectly to feeding device 71, 71A. At least a part of the fluid is then used for the operation of vibration generator 77, 77A and feeding device 71, 71A, for example is routed from vibration generator 77, 77A to feeding device 71, 71A, so that the fluid exerts pressure on feeding device 71, 71A and drives it. The advantage of this embodiment consists in particular in the fact that it is ensured that the filling compound is always subjected to vibration when the filling compound is being fed, so that optimum feeding, delivery, introduction into the cavity and shaping of the filling compound is guaranteed.

The connection between vibration generator 77, 77A and feeding device 71, 71A can at least comprise hollow vibration shaft 86, through the internal space whereof the fluid portion driving feeding device 71, 71A can be routed to feeding device 71, 71A. Vibration shaft 86 emerges into a chamber 89, in which at least a part of feeding device 71, 71A, for example a part of the piston rod or the piston head, is disposed of a mobile manner. Vibration generator 77, 77A with hollow vibration shaft 86 and feeding device 71, 71A are disposed along a common axis. Feeding device 71, 71A, in particular feeding element 82, is preferably disposed concentrically in handgrip 60.

It also emerges from this construction that, apart from switching on or switching off vibration generator 77, 77A and light emission device 63, switching device 68, 68A already described above, in particular valve 73, also activates or stops feeding device 71, 71A, in that it opens or closes the compressed air supply through line 85. To advantage, therefore, feeding of filling compound is completely eliminated when light emission device 63 is activated.

Figure 13:
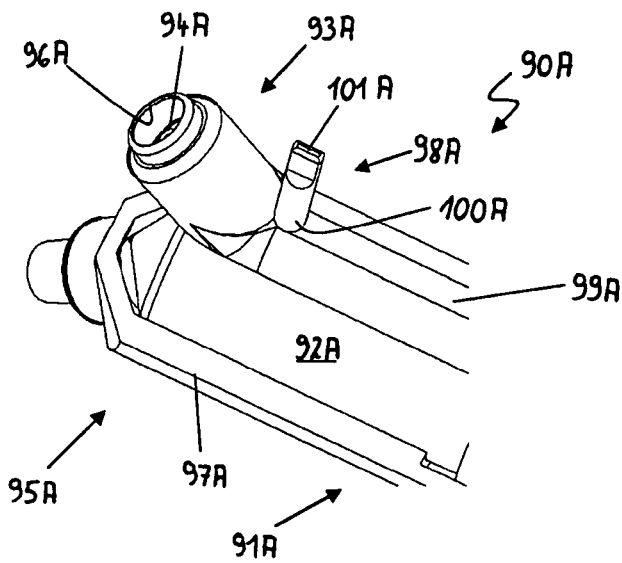
FIG. 13 shows the front end of a dental handgrip for the delivery of filling compound with a first embodiment of a probe for the shaping and smoothing of the filling compound.
Figure 14:
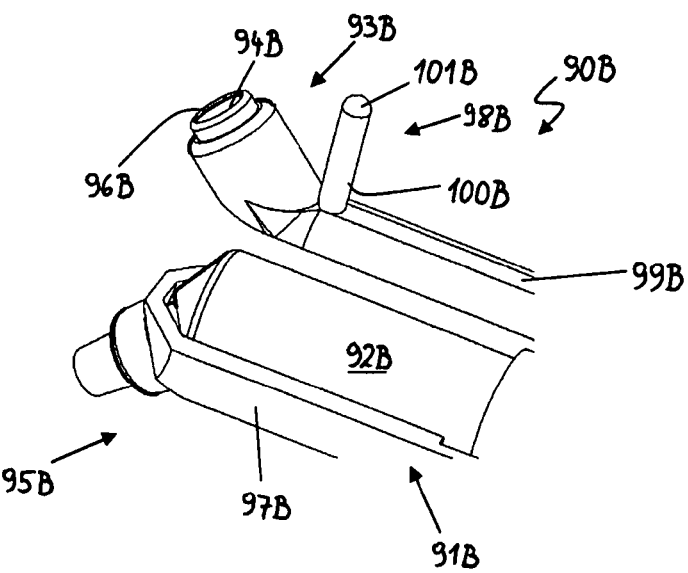
FIG. 14 shows the front end of a dental handgrip for the delivery of filling compound with a second embodiment of a probe for the shaping and smoothing of the filling compound.
Figure 15:
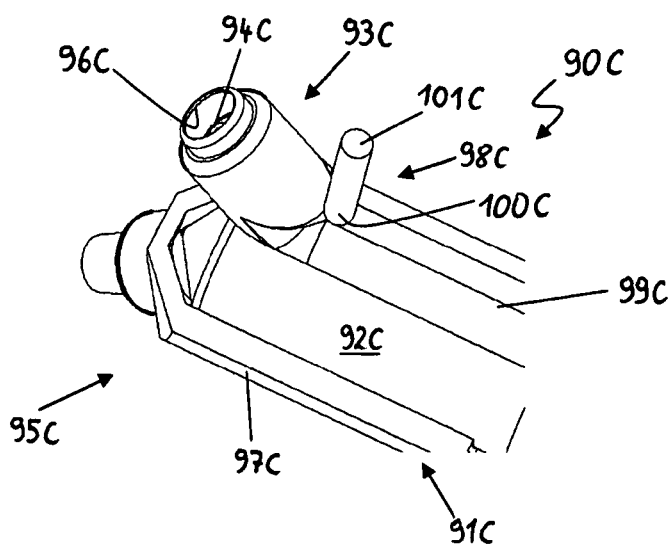
FIG. 15 shows the front end of a dental handgrip for the delivery of filling compound with a third embodiment of a probe for the shaping and smoothing of the filling compound.

FIGS. 13-15 show first ends 95A, 95B, 95C of three dental handgrips 90A, 90B, 90C. Handgrips 90A, 90B, 90C are similar or equal in construction to handgrips 30, 60: They have a light emission device 93A, 93B, 93C disposed at first end 95A, 95B, 95C which comprises at least one LED 94A, 94B, 94C and at least one light emission area 96A, 96B, 96C for the directed radiation emission onto the preparation site, in particular onto the filling compound to be hardened, and a connection device 91A, 91B, 91C to which a container 92A, 92B, 92C for the filling compound can be or is connected. In turn, connection device 91A, 91B, 91C preferably comprises a sonotrode 97A, 97B, 97C.

In addition, there are provided at first ends 95A, 95B, 95C of handgrips 90A, 90B, 90C probes 98A, 98B, 98C, which are used in particular to compact and shape the filling compound before hardening. Probes 98A, 98B, 98C are preferably disposed on handgrips 90A, 90B, 90C in such a way that the filling compound in the tooth cavities is readily accessible with probes 98A, 98B, 98C, without other components of handgrips 90A, 90B, 90C impairing or restricting the handling of probes 98A, 98B, 98C. For this purpose, probes 98A, 98B, 98C are particularly preferably fixed on a carrier device, in particular on rod-shaped carrier 99A, 99B, 99C on which light emission device 93A, 93B, 93C is also fixed.

Probes 98A, 98B, 98C comprise a connection part 100A, 100B, 100C for the connection to handgrips 90A, 90B, 90C and a working part 101A, 101B, 101C. In particular, working parts 101A, 101B, 101C can have different geometries: The spatula-shaped working part 101A of probe 98A following cylindrical connection part 100A is designed essentially parallelepiped-shaped and has at the front end a wedge-shaped, tapering section. Working part 101B of probe 98B has a round, hemispherical shape, working part 101C of probe 98C being formed as an essentially flat plane. Depending on the work to be carried out with the probes and the user's preferences, other geometrical configurations of the working parts of the probes are of course also possible. Probes 98A, 98B, 98C are preferably connected detachably to handgrips 90A, 90B, 90C, in particular to the carrier devices, so that they can be exchanged by the user.

To advantage, handgrips 90A, 90B, 90C can thus be used to perform three functions, i.e., the filling of filling compound into a cavity, the post-treatment of the filling compound with probes 98A, 98B, 98C and the hardening of the filling compound. In a preferred embodiment the probes 98A, 98B, 98C are connected directly or indirectly to a vibration generator 47, 47A, 77, 77A so that they can be set vibrating, which further improves the post-treatment of the filling compound.

Figure 16:
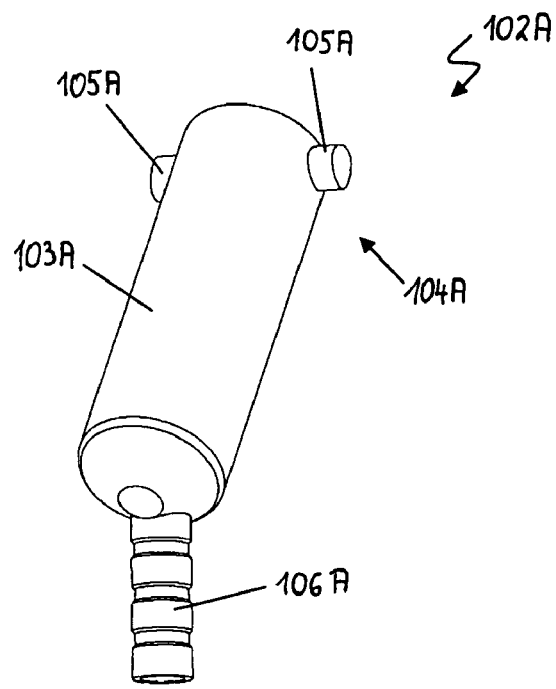
FIG. 16 shows a first embodiment of a container for the filling compound with a flexible cannula.
Figure 17:
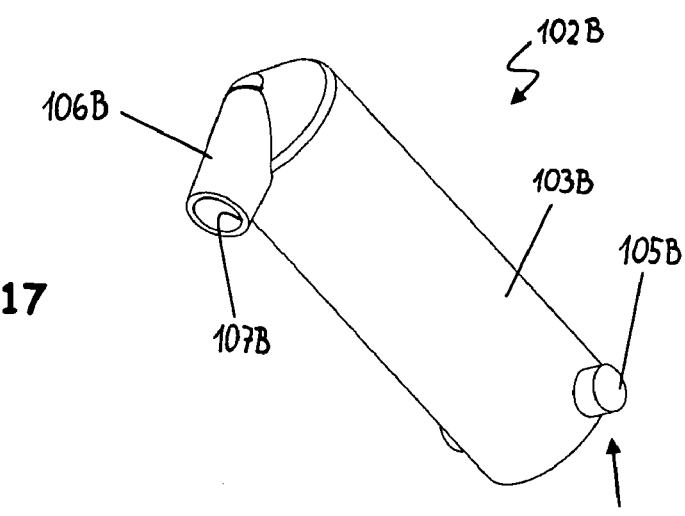
FIG. 17 shows a second embodiment of a container for the filling compound with a short cannula, which is disposed approximately at right angles to the container body.
Figure 18:
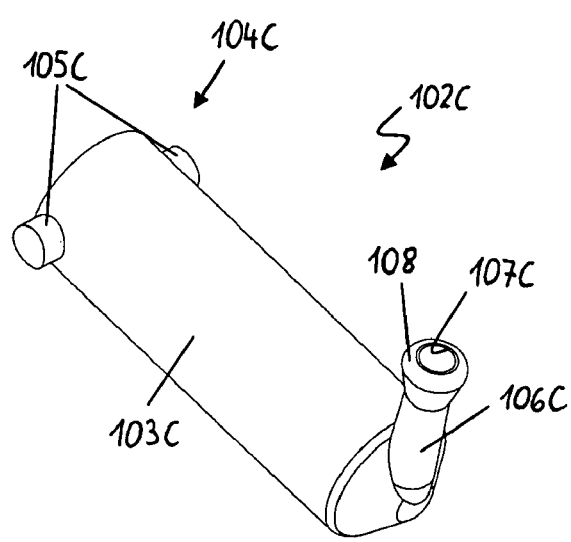
FIG. 18 shows a third embodiment of a container for the filling compound with a long cannula with a thickened front end.

FIGS. 16-18 show filling compound containers 102A, 102B, 102C, which can be connected to handgrips 10, 30, 60, 90. Filling compound containers 102A, 102B, 102C comprise a body 103A, 103B, 103C, which has a hollow space inside in which the filling compound is accommodated. Located at one end of body 103A, 103B, 103C is a connection device 104A, 104B, 104C for the connection of container 102A, 102B, 102C to a dental handgrip 10, 30, 60, 90. Connection device 104A, 104B, 104C comprises two extensions 105A, 105B, 105C, which can be inserted into a bayonet connection of dental handgrips 10, 30, 60, 90. Connection device 104A, 104B, 104C can however also have other configurations, for example as an annular flange or as an offset.

Bodies 103A, 103B, 103C are followed by a delivery tube or a cannula 106A, 106B, 106C, through which the filling compound can be introduced in a targeted manner into the cavity. The cannula usually stands at an angle of approximately 45°—related to the longitudinal axis of filling compound container 102A, 102B, 102C—from the body. As a result, however, cavities of teeth located farther back in the oral cavity, in particular, can only be filled with difficulty. The angle of 45° is however necessary, because otherwise the very viscous filling compound cannot be fed reliably and uniformly from filling compound containers 102A, 102B, 102C.

Surprisingly, however, it has been found in tests that, when use is made of handgrips with vibration generators such as are represented for example in the description to FIGS. 5-10, the viscosity of the filling compound diminishes in such a way that delivery tubes 106A, 106B, 106C can also be fixed to body 103A, 103B, 103C at other angles between 45° up to approximately 90°. This greatly facilitates the introduction of the filling compound into the cavities for the user.

FIGS. 17 and 18 show two filling compound containers 102B, 102C with delivery tubes 106B, 106C disposed approximately at 90°. Delivery tube 106B is comparatively short, so that its projects only slightly, approx. 2.0-3.0 mm, beyond body 103B and has a large delivery opening 107B with a diameter of approx. 2.7-3.4 mm. Filling compound container 102B can accordingly be used in particular for filling larger, two-dimensionally extending cavities.

Delivery tube 106C is longer and projects approx. 4.0-6.0 mm beyond body 103C. The diameter of delivery opening 107C amounts to approx. 1.3-1.8 mm. Filling compound container 102C can therefore be used for smaller or deeper cavities. In addition, the front end of delivery tube 106C is designed thickened, with a diameter increasing in the direction of delivery opening 107C. This stamp 108 is used in particular for compacting and shaping the filling compound introduced into the tooth cavity.

Delivery tube 106A of filling compound container 102A is designed flexible, so that it can advantageously assume different angles—in relation to the longitudinal axis of filling compound container 102A. This further facilitates the introduction of the filling compound into the tooth cavity for the user and saves the manufacturer from having to produce different filling compound containers with delivery tubes at different angles. The flexibility or deformability of filling tube 106A can be achieved by the most diverse measures, for example by the production at least of delivery tube 106A from a flexible material such as plastic, in particular from polyamide, or by the structure of delivery tube 106A, in particular by the fact that delivery tube 106A has different wall thicknesses, as shown in FIG. 16, or by the fact that a flexible internal tube is surrounded by a spiral, spring-loaded supporting element or by the fact that delivery tube 106A has a bellows-like structure.

FIGS. 19-21 illustrate three vibration transmitters or sonotrodes 116A, 116B, 116C, which can be used for example as part of connection devices 31, 60 of handgrips 30, 60. Sonotrodes 116A, 116B, 116C comprise a holder, into which a filling compound container can be inserted. The holder is designed in particular as an elongated holder 117A, 117B, 117C with a base 118A, 118B, 118C and an edge 119A, 119B, 119C running around the latter.

Located at one end of sonotrodes 116A, 116B, 116C is a connection device 120A, 120B, 120C for the connection of sonotrodes 116A, 116B, 116C to a dental handgrip 10, 30, 60, 90. Connection device 120A, 120B, 120C comprises two extensions 121A, 121B, 121C, which can be inserted into a bayonet connection of dental handgrips 10, 30, 60, 90. Connection device 120A, 120B, 120C can however also be designed differently, for example as a plug-in connection, a clamp connection or a screw connection.

Each base 118A, 118B, 118C is divided into a first and second section, the internal diameters or wall thicknesses of which are different and which are connected by a step 122A, 122B, 122C. In order to bring about good feedability of the filling compound, especially during the exit from the filling compound containers, a transmission of the vibrations to the filling compound that is as efficient as possible is required, which is achieved by a narrow, fixed contact between sonotrodes 116A, 116B, 116C and the filling compound containers. This narrow contact is ensured especially in section 123A, 123B, 123C with the narrower internal diameter, the internal diameter or the internal dimension of section 123A, 123B, 123C being the same or even somewhat smaller than a filling compound container usable with sonotrode 116A, 116B, 116C.

Section 123A, 123B, 123C is followed by a tube 124A, 124B, 124C, into which a delivery tube or a cannula of a filling compound container can be introduced. Corresponding to the aforementioned different embodiments of the cannula, tubes 124A, 124B, 124C can also be designed differently and can in particular have a different length, a different diameter or a different angle of inclination, in particular between 45° up to approx. 90° in relation to the longitudinal axis of sonotrodes 116A, 116B, 116C. Tube 124A, 124B, 124C can also have at its free end reinforcements or thickened portions for compacting the filling compound.

The devices and appliances are not restricted to the presented field of application and the described example of embodiment, but rather include all possible embodiments that do not change the functional principle in its essence and logic. Thus, the vibration generator can also be designed as an electrically operated vibration generator, for example as a piezoelement or as a magnetostrictive element. If the light emission device comprises a light source disposed in the handgrip, in particular an optical semiconductor element, the vibration generator and the light source can also be connected to a common energy source in a preferred example of embodiment. Two circuits may then possibly be necessary in order to make the different required current parameters available to the electrically operated vibration generator and the light source.

What is claimed is:

1. A dental handgrip for delivering filling compound into a tooth cavity, comprising:
   a first end;
   a second end opposite the first end;
   a body extending between the first end and the second end;
   a connection device which releasably holds a filling compound container,
   a light emission device operable to provide radiation having a wavelength and radiant power for hardening of filling compound, and
   a safety device operable to prevent premature or inadvertent light emission onto the filling material, wherein
   the connection device is disposed at the first end of the handgrip, wherein
   the dental handgrip comprises a feeding device operable to feed filling compound from the filling compound container, and wherein the safety device comprises a switching device switchable between a first mode allowing the feeding device to be operated to feed the filling compound and preventing the light emission device from irradiating the treatment site, and a second mode allowing the light emission device to irradiate the treatment site and preventing the feeding device from feeding filling compound to the treatment site.

2. The dental handgrip according to claim 1, further comprising:
   a coupling element on the handgrip operable to connect the light emission device to an external light source or an external energy source, the coupling element being configured for coupling to a counter-coupling element provided for connecting a dental hand-held instrument with another function.

3. The dental handgrip according to claim 1, wherein
   the light emission device comprises at least one of a light guide and a light source.

4. The dental handgrip according to claim 3, wherein
   the light source comprises an optical semiconductor element.

5. The dental handgrip according to claim 1, wherein
   the light emission device defines at least one light emission area positioned nearer the first end than the second end of the handgrip.

6. The dental handgrip according to claim 1, wherein
   the connection device is configured such that the a delivery opening of the filling compound container through which filling compound can be delivered to a treatment site points in a first direction, and wherein the safety device comprises a light emission area defined by the light emission device pointing in a direction different from the first direction.

7. The dental handgrip according to claim 1, wherein
   the light emission device is movably connected to the dental handgrip between a first advanced position, where the light emission device is disposed near the first end of the handgrip, and a second retracted position, where the light emission device is disposed remote from the first end of the handgrip, and wherein the handgrip comprises an actuator disposed on the outside of the handgrip, said actuator being connected to the light emission device, the light emission device being movable between the first advanced position and the second retracted position by operating said actuator.

8. The dental handgrip according to claim 1, wherein
   the safety device comprises a rotatable or swivelling cover device configured to selectively cover a light emission area defined by the light emission device and a delivery opening of the filling compound container through which filling compound can be delivered to a treatment site.

9. The dental handgrip according to claim 1, wherein
   the switching device comprises at least one common switching element for the feeding device and the light emission device.

10. The dental handgrip according to claim 1, wherein the switching device comprises at least one of electrical switching contacts and a valve.

11. The dental handgrip according to claim 1, further comprising:
    a probe connectable to the body of the handgrip and configured to project away from the handgrip, the probe being shaped for use in manipulating filling compound that has been fed to a treatment site, wherein the probe comprises a free end for manipulating filling compound, said free end being separated from a delivering opening for the filling compound.

12. The dental handgrip according to claim 11, wherein
    the handgrip comprises a vibration generator, and the vibration generator is operatively coupled to the probe to selectively cause the probe to vibrate.

13. A dental handgrip for delivering filling compound into a tooth cavity, comprising:
    a first end.
    a second end opposite the first end;
    a body extending between the first end and the second end;
    a connection device which releasably holds a filling compound container,
    a light emission device operable to provide radiation having a wavelength and radiant power for hardening of filling compound, and
    a safety device operable to prevent premature or inadvertent light emission onto the filling material, wherein
    the connection device is disposed at the first end of the handgrip, wherein
    the dental handgrip comprises a vibration generator to subject filling compound in the connected filling compound container to vibration in order to reduce the viscosity of the filling compound, wherein the filling compound does not pass through the vibration generator, and the safety device comprises a switch that is switchable to allow operation of one of the vibration generator and the light emission device.

14. The dental handgrip according to claim 13, wherein the switching device comprises at least one common switching element for the vibration generator and the light emission device.

15. The dental handgrip according to claim 13, wherein the switching device comprises at least one of electrical switching contacts and a valve.

16. The dental handgrip according to claim 13, wherein the switching device comprises a switching element with a guide slot, the switching element being movably coupled to the body of the handgrip, a valve body accommodated in a mobile manner in the handgrip and having electrical contacts connected to the switching element, an eccentrically disposed guide pin being provided on the valve body and engageable in the guide slot.

17. The dental handgrip according to claim 13, wherein the connection device is configured such that a delivery opening of the filling compound container through which filling compound can be delivered to a treatment site points in a first direction, and wherein the safety device comprises a light emission area defined by the light emission device pointing in a direction different from the first direction.

18. The dental handgrip according to claim 13, wherein the light emission device is movably connected to the dental handgrip between a first advanced position, where the light emission device is disposed near the first end of the handgrip, and a second retracted position, where the light emission device is disposed remote from the first end of the handgrip, and wherein the handgrip comprises an actuator disposed on the outside of the handgrip, said actuator being connected to the light emission device, the light emission device being movable between the first advanced position and the second retracted position by operating said actuator.

19. A dental handgrip for delivering filling compound into a tooth cavity, comprising:
- a connection device, which releasably holds a filling compound container;
- a light emission device operable to provide radiation having a wavelength and radiant power for hardening of filling compound; and
- a safety device operable to prevent premature or inadvertent light emission onto the filling material, wherein the dental handgrip comprises a feeding device operable to feed filling compound from the filling compound container, wherein the safety device comprises a switching device switchable between a mode allowing the feeding device to be operated to feed the filling compound and a second mode allowing the light emission device to be operated, and wherein the switching device comprises a switching element with a guide slot, the switching element being movably coupled to the handgrip, a movable valve body accommodated in the handgrip and having electrical contacts connected to the switching element, an eccentrically disposed guide pin being provided on the valve body and engageable in the guide slot.

20. A dental handgrip for delivering filling compound into a tooth cavity comprising:
- a connection device, to which a filling compound container is connectible,
- a fluid-operated feeding device operable to feed the filling compound from the filling compound container when the filling compound container is connected; and
- a fluid-actuated vibration generator to selectively transmit vibrations to the filling compound to assist in feeding the filling compound to the treatment site, said fluid-actuated vibration generator being arranged in the handgrip, so that the vibrations generated by the vibration generator can be transmitted up to a delivering opening from which the filling compound is delivered to the treatment site, and wherein the handgrip is designed such that the fluid which actuates the vibration generator does not suck the filling compound out of the filling compound container.

21. The dental handgrip according to claim 20, further comprising:
- a coupling element for the connection of the feeding device to an external fluid source, the coupling element preferably been designed in such a way that it can be coupled to a counter-coupling element, which is provided for the connection to a dental hand-held instrument with another function.

22. The dental handgrip according to claim 20, wherein the feeding device comprises a feeding element displaceable by the fluid in the direction of the connection device, wherein the feeding element is configured to push the filling material out of the filling compound container.

23. The dental handgrip according to claim 22, wherein the vibration generator and the displaceable feeding element are connected to one another directly or indirectly, so that at least a part of the fluid can be used for the operation of the displaceable feeding element and the vibration generator.

24. The dental handgrip according to claim 23, wherein a common fluid line is provided for the vibration generator and the displaceable feeding element.

25. The dental handgrip according to claim 22, wherein the vibration generator comprises a hollow vibration shaft, through the interior space whereof the fluid portion driving the displaceable feeding element can be routed to the displaceable feeding element.

26. The dental handgrip according to claim 25, wherein the vibration shaft emerges into a chamber, in which at least a part of the feeding device is disposed.

27. The dental handgrip according to claim 20, wherein a blocking element is provided for interrupting the fluid delivery to the feeding device and/or to the vibration generator.

28. The dental handgrip according to claim 20, further comprising
- a light emission device via which radiation having a wavelength and radiant power for hardening of filling material can be provided.

29. The dental handgrip according to claim 20, wherein the fluid-actuated vibration generator is operatively coupled to the connection device to transmit vibrations via the connection device to the filling compound, said connection device being arranged at a front end of the handgrip, the front end being near the delivering opening.

30. A dental handgrip for delivering filling compound into a tooth cavity comprising:
- a connection device, which releasably holds a filling compound container,
- a fluid-operated feeding device operable to feed the filling compound from the filling compound container when the filling compound container is connected; and
- a fluid-actuated vibration generator to selectively transmit vibrations to the filling compound to assist in feeding the filling compound to the treatment site, said fluid-actuated vibration generator being arranged in the handgrip, so that the vibrations generated by the vibration generator can be transmitted up to a delivering opening from which the filling compound is delivered to the treatment site, wherein a common fluid line is provided for the vibration generator and the fluid-operated feeding device.

* * * * *

UNITED STATES PATENT AND TRADEMARK OFFICE
CERTIFICATE OF CORRECTION

PATENT NO. : 7,857,621 B2  
APPLICATION NO. : 11/985873  
DATED : December 28, 2010  
INVENTOR(S) : Gunter Teufelberger and Hannes Wagner It is certified that error appears in the above-identified patent and that said Letters Patent is hereby corrected as shown below:

<u>In the Specification:</u>

Column 4, line 31, "embodiment" should read --embodiments--.

Column 6, line 18, "tube 5" should read --tool 5--.

Column 6, line 48, "for the operation which" should read --for the operation of which--.

Column 6, line 62, "probe 8 which" should read --probe 8, which--.

Column 9, line 24, "79; an" should read --79, an--.

Column 13, line 58, "its projects" should read --it projects--.

Column 14, line 24, "31, 60" should read --31, 61--.

<u>In the Claims:</u>

Claim 13, column 16, line 38, "end." should read --end;--.

Claim 13, column 16, lines 55-56, "to allow" should read --to alternatingly allow--.

Claim 21, column 18, lines 4-5, "preferably been designed" should read --preferably designed--.

Signed and Sealed this  
Twenty-eighth Day of June, 2011

David J. Kappos  
*Director of the United States Patent and Trademark Office*